US00PP25200P3

(12) United States Plant Patent
Pavlich

(10) Patent No.: US PP25,200 P3
(45) Date of Patent: Dec. 30, 2014

(54) *BEGONIA* PLANT NAMED 'GARDEN ANGEL SILVER'

(50) Latin Name: ***Begonia* hybrid**
Varietal Denomination: Garden Angel Silver

(71) Applicant: Terra Nova Nurseries, Inc., Canby, OR (US)

(72) Inventor: John C. Pavlich, Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 97 days.

(21) Appl. No.: 13/986,505

(22) Filed: May 9, 2013

(65) Prior Publication Data

US 2014/0338085 P1 Nov. 13, 2014

(51) Int. Cl.
*A01H 5/00* (2006.01)

(52) U.S. Cl.
USPC ..... Plt./343

(58) Field of Classification Search
USPC ..... Plt./343
See application file for complete search history.

*Primary Examiner* — Annette Para
(74) *Attorney, Agent, or Firm* — Klarquist Sparkman, LLP

(57) ABSTRACT

A new and distinct form of *Begonia* plant characterized by maple-like palmately lobed leaves with showy interveinal silvering, red leaf backs, a bushy habit, small clusters of large cherry pink flowers in winter to early spring, hardy to USDA Z7, and excellent vigor.

1 Drawing Sheet

Botanical denomination: *Begonia* hybrid.

Variety designation: 'Garden Angel Silver'.

Parentage: *Begonia* 'Benitochiba'×*Begonia grandis* subsp. *evansiana.*

Comparison to siblings *Begonia* 'Garden Angel Plum' U.S. application Ser. No. 13/986,507 and *Begonia* 'Garden Angel Blush' U.S. application Ser. No. 13/986,504.

BACKGROUND OF THE INVENTION

The present invention relates to a new and distinct cultivar of *Begonia*, of the family Begoniaceae, and given the cultivar name, 'Garden Angel Silver'. This plant originated from planned breeding program for a colorful series of landscape *Begonia.* The new cultivar originated from a cross between *Begonia* 'Benitochiba' (unpatented), as the seed parent, and *Begonia grandis* subsp. *evansiana* (unpatented), as the pollen parent. This selection is uniquely characterized by:

1. maple-like palmately lobed leaves with showy interveinal silvering,
2. red leaf backs,
3. a bushy habit,
4. small clusters of large cherry pink flowers in winter to early spring,
5. hardy to USDA Z7, and
6. excellent vigor.

Compared to the seed parent *Begonia* 'Benitochiba', the new cultivar has leaves that are silver rather than purple blushed and are palmately lobed rather than palmately compound. The new cultivar is hardy rather than being a tropical plant.

Compared to the pollen parent, *Begonia grandis* subsp. *evansiana* (common name the Hardy *Begonia*), the new cultivar has leaves that are palmately lobed rather than no lobes and with strong interveinal silvering rather than no silvering.

Compared to *Begonia* 'Garden Angel Plum' (U.S. Plant patent application Ser. No. 13/986,507), the new cultivar is silver interveinally rather than being all plum interveinally and is shorter.

Compared to *Begonia* 'Garden Angel Blush' (U.S. Plant patent application Ser. No. 13/986,504), the new cultivar is all silver interveinally rather than having plum-red violet blush.

The new variety has been reproduced only by asexual propagation (cuttings and tissue culture). Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the flowers and leaves of *Begonia* 'Garden Angel Silver' in January in Canby, Oreg.

FIG. 2 shows a 9 month old plant in a growing in a one gallon container in August in Canby. Oreg.

DETAILED PLANT DESCRIPTION

The following is a detailed description of the new *Begonia* cultivar based on observations of nine-month-old specimens grown in one gallon containers inside a cool greenhouse in early January in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on The Royal Horticultural Society Colour Chart, $5^{th}$ edition.

Plant:

*Type.*—Herbaceous rhizomatous perennial.

*Form.*—Caulescent, shrubby.

*Cold hardiness.*—USDA Zone 7.

*Size.*—Grows to 57 cm tall and 60 cm wide.

*Vigor.*—Excellent.

Stem:

*Type.*—Upright.

*Size.*—Grows to 24 cm long and 10 mm wide.

*Internodes.*—From 1 cm to 8 cm long.

*Surface.*—Pubescent.

*Color.*—Greyed Purple 187B.

Leaf:

*Type.*—Simple.

*Arrangement.*—Alternate.

*Shape.*—Broadly ovate.

*Lobing/division.*—4 to 6 main palmate lobes.

*Margins.*—Serrate.

*Venation.*—Palmate, Grayed Green 197'A on topside, bottom side Red Purple 59A.

*Apex.*—Acuminate.

*Base.*—Oblique.

*Blade size.*—10 cm to 13.5 cm wide and 13.5 cm long.

*Surface texture.*—Pubescent on top and bottom.

*Stipules.*—Deciduous, ovate-lanceolate, grows to 16 mm long and 7 mm wide, papery, translucent, glabrous on both sides, Greyed Red 181 A.

*Petiole description.*—Grows to 13.5 cm long and 6 mm wide, pubescent, Greyed Brown N199A.

*Leaf color.*—Top side Black 202B except along veins where closest to Green N137A; bottom side Red Purple 59A.

Inflorescence:

*Type.*—Axillary, bisexual, cymose.

*Number of flowers per cyme.*—2 to 5.

*Peduncle description.*—Grows 12 cm long and 3 mm wide, glabrous, fleshy, Yellow Green 152A; with 2 opposite, dehiscent petiolate leaf-bracts below each cyme, which grow to 5 mm wide and 16 mm long, margins entire, tip apiculate, both sides glabrous Greyed Purple 185C.

*Pedicel description.*—Grow to 28 mm long, 1.5 mm wide, fleshy, sparsely pubescent, Greyed Purple 185C on staminate and pistillate flowers.

*Bloom period.*—Late fall to early winter in Canby, Oreg.

Flower bud:

*Size.*—Staminate flowers 16 mm long and 12 mm wide prior to opening; pistillate flowers are 24 mm deep and 28 mm wide prior to opening.

*Color.*—Red Purple 67A on tepal area, Red 48B on ovary.

Flower:

*Type.*—Monoecious, bilaterally symmetrical.

*Pistillate flower.*—Grows to 26 mm deep and 52 mm wide overall; 5 fleshy tepals, grow to 26 mm long and 14 mm wide, broadly elliptical, tip acute, base attenuate, margins entire, glabrous on inside and pubescent on outside, Red Purple 62B on inside and 62A on back side; ovary to 30 mm wide and 13 mm deep, three winged, two equal and one longer, Red 48B, style 5 mm long and 3 mm to 4 mm wide, Yellow 11A, stigma 3 branched and twisted, stigma 5 mm deep and 10 mm wide overall, Yellow 11A.

*Staminate flower.*—10 mm deep and 48 mm wide, 4 tepals, 2 larger outer tepals grow to 24 mm long and 16 mm wide, ovate, margin entire, tip obtuse, base cuneate; inner tepals grow to 22 mm long and 11 mm wide, oblanceolate, entire, tip obtuse, base cuneate; tepals topside Red Purple N66D, bottom side Red Purple N66C; stamen many in a globular head 6 mm in diameter on staminal column 1.5 mm long and 1 mm wide, Yellow 3C; filaments threadlike and 3 mm long, Green Yellow 1D, anthers 1.5 mm long, anthers Yellow 13B, no pollen.

*Fragrance.*—None.

*Lastingness.*—A cyme blooms for about 4 weeks on the plant.

Fruit and seed: None, sterile.

Diseases and pests: The new cultivar is typical to the genus. No known resistances to pests or diseases. No problems have been found in Canby, Oreg.

I claim:

1. A new and distinct form of *Begonia* plant as hereby illustrated and described.

* * * * *

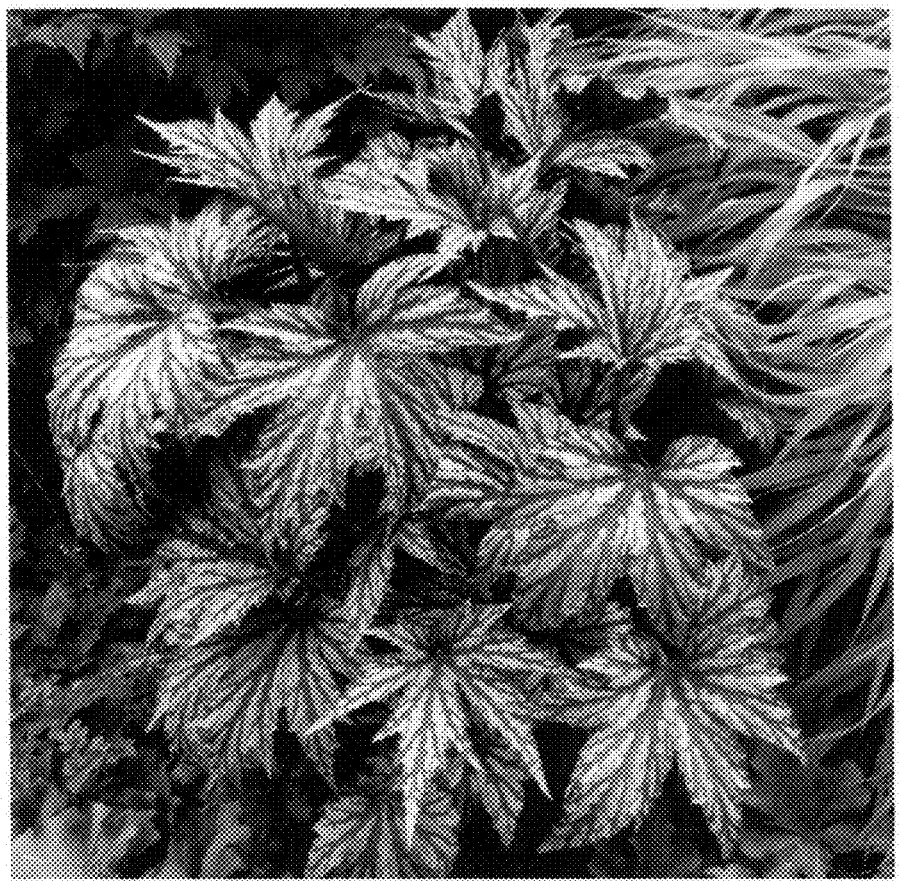

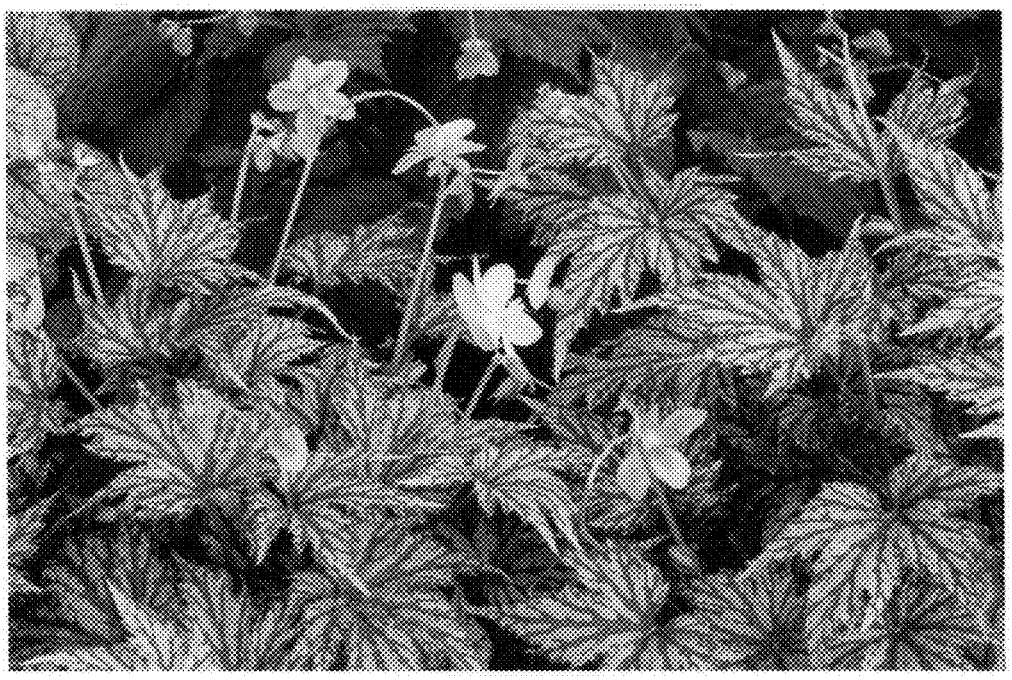
FIG.1 above, FIG. 2 below